US009140712B2

(12) United States Patent
Sofer

(10) Patent No.: US 9,140,712 B2
(45) Date of Patent: Sep. 22, 2015

(54) IMMUNE AND OXYGEN SYSTEM MEASURING AND DRUG SCREENING METHOD AND APPARATUS

(76) Inventor: Samir Sofer, Clifton, NJ (US)

( * ) Notice: Subject to any disclaimer, the term of this patent is extended or adjusted under 35 U.S.C. 154(b) by 0 days.

(21) Appl. No.: 13/695,150

(22) PCT Filed: Apr. 27, 2011

(86) PCT No.: PCT/US2011/034051
§ 371 (c)(1),
(2), (4) Date: Oct. 29, 2012

(87) PCT Pub. No.: WO2011/139733
PCT Pub. Date: Nov. 10, 2011

(65) Prior Publication Data
US 2013/0041239 A1    Feb. 14, 2013

Related U.S. Application Data

(60) Provisional application No. 61/328,409, filed on Apr. 27, 2010.

(51) Int. Cl.
*G01N 33/84* (2006.01)
*A61B 5/145* (2006.01)
*A61B 5/1455* (2006.01)
*G01N 33/48* (2006.01)

(52) U.S. Cl.
CPC .............. *G01N 33/84* (2013.01); *A61B 5/145* (2013.01); *A61B 5/1455* (2013.01); *G01N 33/48* (2013.01)

(58) Field of Classification Search
CPC ...... A61B 5/145; A61B 5/1455; G01N 33/48; G01N 33/49
USPC ......... 600/300, 309, 310, 345, 347, 365, 473, 600/476; 435/2, 5, 288.7; 73/31.05, 23.2; 422/82.01–82.09, 83–84, 98; 604/19–24, 48
See application file for complete search history.

(56) References Cited

U.S. PATENT DOCUMENTS

| | | | | |
|---|---|---|---|---|
| 4,041,933 A | * | 8/1977 | Reichenberger | 600/357 |
| 5,398,682 A | * | 3/1995 | Lynn | 600/335 |
| 5,720,284 A | * | 2/1998 | Aoyagi et al. | 600/322 |
| 6,074,607 A | | 6/2000 | Slovacek et al. | |

(Continued)

FOREIGN PATENT DOCUMENTS

| | | |
|---|---|---|
| EP | 1 110 562 A2 | 6/2001 |
| EP | 1 110 562 A3 | 6/2004 |
| SU | 1739295 A1 | 8/1989 |

OTHER PUBLICATIONS

McKenna: An Investigation of the Oxygraphic Response of Stressed Bovine Blood; Internet Cite May 1, 1997; p. 159.

(Continued)

*Primary Examiner* — Tse Chen
*Assistant Examiner* — Chu Chuan (JJ) Liu
(74) *Attorney, Agent, or Firm* — Sara C. Kanos; Nexsen Pruet, LLC

(57) ABSTRACT

Method and apparatus for monitoring health as related to immune system function, and for measuring the effects of toxins and other stresses. A method for pre-screening drugs for the pharmaceutical pipeline. A method for using an Immunogram as a research tool. A method for preparing compounds or drugs for treatment, therapy, or cure of diseases.

15 Claims, 6 Drawing Sheets

(56) References Cited

U.S. PATENT DOCUMENTS

| | | | |
|---|---|---|---|
| 6,532,958 B1* | 3/2003 | Buan et al. | 600/323 |
| 6,925,852 B2* | 8/2005 | Susko | 73/23.2 |
| 7,025,734 B1* | 4/2006 | Ellis et al. | 600/345 |
| 2004/0133079 A1 | 7/2004 | Mazar et al. | |
| 2004/0133086 A1 | 7/2004 | Ciurczak et al. | |
| 2006/0074607 A1 | 4/2006 | Weller | |
| 2006/0171845 A1* | 8/2006 | Martin et al. | 422/82.07 |
| 2008/0096805 A1* | 4/2008 | Tye | 514/6 |

OTHER PUBLICATIONS

Sofer, Samir et al; "ROX and BOX: new tools for detecting patient injury and drug toxicity"; Jun. 15, 2010; Internet cite.

McKenna et al; Comparative Hemotology International; "Molecular Oxygen Peaks (MOPs) in Blood: Their Discovery, Investigation and Implications"; 1999.

* cited by examiner

US 9,140,712 B2

IMMUNE AND OXYGEN SYSTEM MEASURING AND DRUG SCREENING METHOD AND APPARATUS

PRIORITY CLAIM

The present application claims the benefit of priority of U.S. Provisional Application No. 61/328,409, filed on Apr. 27, 2010, which is incorporated herein in its entirety.

BACKGROUND OF THE INVENTION

The immune and oxygen system is a vital part of the body's functions and defense mechanism against illness and disease for animals and humans. Really any living thing, including plants and microorganisms utilize an internal system for combating stress and adversity. This system's ability to respond to disease, supply energy to tissues, detoxify the body against pollution and drugs, conduct neuromuscular signaling, etc., varies from individual to individual and from day to day within the same individual. This system will be briefly referred to herein as "the immune system."

For example, a patient suffering from Hepatitis C, cancer, other disease, or even a physical or psychological stress, may have a taxed immune system. Certain immunotherapy drugs designed to boost or modulate the immune system, such as Interferon for Hepatitis C, or cytokines and/or activated T-cells for cancer, help the individual's immune system to fight a given disease. Interferon, for example, can help an individual fight Hepatitis C. However, not all individuals respond to the same extent to immunotherapy.

The distinction among responses to immunotherapy was shown in a clinical study for evaluating Hepatitis C patients on Interferon treatment, as approved by the Institutional Review Board of the University of Medicine and Dentistry of New Jersey. In summary of this study, the existence of non-responders to Interferon treatment of Hepatitis C patients is well known. A review is provided by Dr. William M. Lee at the University of Texas Southwestern Medical School. Dr. Lee and colleagues at nine other institutions worked on the HALT-C study from 2002-2007. This study points out that there are 50-60% of non-responders to Interferon plus ribavirin treatment. These non-responders are furthermore non-responsive to long-term Interferon maintenance strategies in the sense that there is no significant difference in the rate of progression of liver disease between non-responders on Interferon and non-responders not on Interferon maintenance. The question that arises from this work is: Why is there a difference between responders and non-responders?

Hinshaw, Sofer, and coworkers (Am. J. Physiol Heart Cir. Phys: H742-750 (1980)) found when studying an extracorporeal blood recirculation system in canine endotoxic shock models, that the shear stress generated by the extracorporeal pump circulation system led to autoanticoagulation. That is, stressed blood would not clot, in the absence of external anticoagulants such as heparin, even in a vigorously agitated blood circulation system. They further isolated from stressed blood, HLF, a heparin-like factor (please see reference to bNOS below), which was shown to prevent clotting. Hinshaw and coworkers (Circ. Shock 1979; 6(3)261-9) also noted that such stressed blood in canines led to a 'cure' in the dogs, the autoanticoagulated dogs, were resistant to shock when injected with bacterial endotoxin.

The inventor here, Sofer, pursued this problem as a New Jersey State Sponsored Research Professor of Biotechnology, and discovered MOPs, or molecular oxygen peaks (not radical oxygen species) emanating from blood that were generated from stressed blood (Comparative Haematology International (1999) 9:68-71). Other published works based on thousands of runs by Sofer's NJIT Biotechnology group reinforce the presence of oxygen peaks generated by many other types of stress: chemical, thermal, pH, etc. The questions that arise here are: Where does the oxygen from the MOPs come from, in view of the fact that the MOPs are generated from blood at zero oxygen concentration, where the hemoglobin equilibrium oxygen content is zero? Why does stress release this oxygen? Why does stress strengthen the immune system against bacterial endotoxin attack? These questions were not clarified by these researchers.

While Sofer's group acknowledged the possibility that the probe they used for oxygen measurements may also read Nitric Oxide or $H_2S$ or other compounds, they did not consider the combined action of oxygen with these compounds, nor did they postulate the existence of NO- or other-reservoirs.

In a thorough review of the literature of NO, Pieper (Hypertension. 1998; 31:1047-1060.) Galen M. Pieper, Review of Alterations in Endothelial Nitric Oxide Production in Diabetes) does not teach that oxygen or NO or others are present in reservoirs, nor does he propose their combined actions. Furthermore, this review fails to consider the rates of change of the concentrations of these materials as a function of time, i.e., the slopes of curves relating to rates of reaction. He points out the inconclusiveness of NO science with respect to many of the major diseases.

Maltepe and Sougstad (Maltepe, Emin; Saugstad, Ola Didrik, Oxygen in Health and Disease: Regulation of Oxygen Homeostasis-Clinical Implications Pediatric Research: March 2009—Volume 65—Issue 3—pp 261-268) offer a detailed review of the role of oxygen in health and disease. They do not consider oxygen or NO or other reservoirs, or their combined actions. Any of the foregoing references cited in the background are incorporated in their entirety herein by reference.

Thus there is a need for a way to assess or quantify the ability of an individual's immune system to ward off disease and to respond to immune system-boosting drugs such as Interferon.

SUMMARY OF THE INVENTION

The following presents a simplified summary of the invention in order to provide a basic understanding of some aspects of the invention. This summary is not an extensive overview of the invention. It is not intended to identify key or critical elements of the invention or to delineate the scope of the invention; its sole purpose is to present concepts of the invention in a simplified form as a prelude to the more detailed description that is subsequently presented.

According to its major aspects and briefly stated, one embodiment of the present invention includes a method comprising the steps of: providing at least one sensor; providing a sample including an amount of bodily fluid or material with an amount of signaling material; determining a baseline value for said amount of signaling material; introducing a stress into said sample; determining by said sensor a value for ROX in said sample; and determining by said sensor a value for BOX in said sample. Furthermore, the present method includes the step of determining changes in concentrations of ROX and BOX over time.

The present invention further includes an apparatus. One embodiment of the apparatus comprises: an optical probe and a membrane probe operatively connected to a processor for computing a value for ROX and a value for BOX in a given sample. The processor of the present invention further computes rates of change in concentrations of ROX and BOX over time. These rates of change are shown by representative slopes.

The present invention further includes a method for controlling the concentrations of ROX and BOX, comprising the steps of: providing at least one sensor; providing a sample or organism including an amount of bodily material with an amount of signaling material; determining a baseline value for said amount of signaling material; introducing a stress into said sample or organism; determining by said sensor a value for ROX in said sample or organism; determining by said sensor a value for BOX in said sample or organism; and introducing a controlling or blocking material into said sample or organism, which can be a patient, wherein said controlling material is capable of altering either said value for ROX or said value for BOX in said sample or organism.

Further, the present invention includes a method for predicting the onsent of rejection to an organ transplant or to a drug, comprising the steps of: providing at least one sensor; providing a sample from a patient intending to undergo treatment, including an amount of bodily material with an amount of signaling material; determining a baseline value for said amount of signaling material; introducing a stress into said sample, wherein said stress includes an amount of treatment material, and wherein said treatment material is a material that is integral to said treatment; determining by said sensor a value for ROX in said sample; and determining by said sensor a value for BOX in said sample.

These and other features and their advantages will be readily apparent to those skilled in the art of evaluating health and readiness for medical treatment from a careful reading of the Detailed Description of Preferred Embodiments, accompanied by the following drawings.

BRIEF DESCRIPTION OF THE DRAWINGS

In the figures.

DETAILED DESCRIPTION OF PREFERRED EMBODIMENTS

Figure 1:
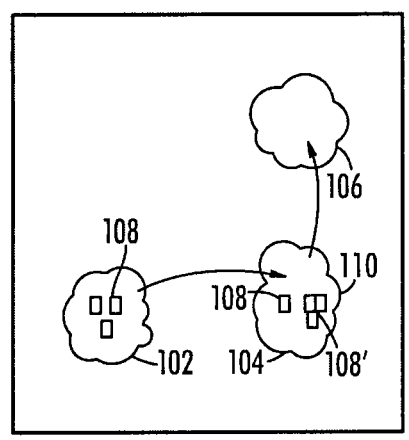
FIG. 1 is a schematic representation of a biological system according to one embodiment of the present invention.

The present invention is a method for determining the status of an apparently healthy individual's immune system to resist attack, a method for determining a patient's response to and ability to respond to immunomodulators, or substances that boost or modify the immune system performance, as a part of immunotherapy in combating diseases such as Hepatitis C, and a method of adjusting the dosage of immunomodulators, particularly those that may be toxic in larger dosages. The present invention further is a method for determining general health information including the potential of an individual to tolerate and overcome internal and external stresses.

The present invention is a method and apparatus for quantifying the ability of an individual's immune system to ward off disease and to be helped in this regard by immune-boosting or modulating drugs such as Interferon. The present invention can also apply to the nervous system, detoxification system, muscular system, and energy production and transfer system of a person.

When used with an internal standard, this method and apparatus may also be utilized for quantifying the toxicity and physiological effects of potential future drugs, as well as other chemicals. As used herein "internal standard" can include any suitable material that can mirror or exhibit the properties or qualities of a sample being tested. For example, the material known as MedX™, which is derived from bovine blood, is a suitable internal standard for comparison with blood samples of patients for purposes of the present invention. Importantly, the use of an internal standard, such as MedX™, facilitates in tracking the history and authenticity of a sample. For example, if a sample is destroyed, and the related internal standard is also destroyed, it can be assumed that both the internal standard and the sample were subjected to similar mishandling or environmental stresses.

The present method and apparatus may also be used for evaluating the usefulness of biomarkers. Furthermore, the method and apparatus may also be used to determine the overall health of an individual, including providing information as to the strength of an individual regarding the ability to receive and overcome stress, disease, and drug therapy.

Without wishing to be bound by theory, it is believed that oxygen, or molecules containing oxygen, such as nitric oxide and other immune system or bodily signaling molecules, such as hydrogen sulfide and others, herein all referred to as "signaling materials," is a significant and potent tool in the body's defense against invading foreign chemicals and organisms. The storage and release of plentiful amounts of signaling materials, particularly oxygen, forms an integral part of the body's immune system.

However, signaling materials, such as oxygen, are soluble in plasma, for example, at very low concentrations. Therefore, the body must transport signaling materials in a mobile, packaged form into the locations of need, such as cuts, tumors, and tissues requiring high amounts of energy. This packaged form of signaling materials is referred to as the reservoir of oxygen (ROX). As used herein, the term "ROX" means oxygen molecules, as well as other signaling materials, including NO and $H_2S$, that are in a packaged or bundled form for effective delivery through blood.

The terms "bundled" and "packaged" are used interchangeably, and refer to any means, such electromagnetic forces or protein wrapping, by which cells in the blood, including white blood cells, concentrate signaling materials, such as oxygen and NO, into a form that is transportable in the blood for use by the systems, such as the immune system, in the body. The measurement of ROX is a measurement of the patient's innate immune viability and how the patient will respond immediately to a given treatment or drug. When ROX is submitted to stress, oxygen molecules are released from the bundled form. As used herein, "stress" is defined as any factor, be it physical, chemical, electromagnetic or other, that alters the existing state or equilibrium of the blood. Furthermore, stress can be a single, full stress, such as a full treatment dosage of a drug, a partial stress, such as a partial treatment dosage, or a stress that is administered more than once over time, such as a full dosage of a treatment drug that is administered multiple times over a period of time.

The ROX in the blood or tissues is the indicator for reserves of signaling materials available in the blood and is stated to be a measure of the innate ability of a person to provide oxygen or other important bodily materials for an attack by invading foreign chemicals and organisms. In addition to serving as a signaling agent for the response to such an attack, ROX, which is released into the blood by stress, supplies signaling materials to needy tissues, for example, for energy. Beyond merely a measurement of hemoglobin, which generally indicates the currently available oxygen in arterial blood, ROX is a measurement of oxygen, NO, and $H_2S$ reservoirs, as well as the reservoirs of other signaling materials, which are present in all components of blood, including plasma and red blood cells. Moreover, the present invention can be used to analyze any bodily fluid, including spinal fluid, which contains reservoirs of signaling materials.

It is further stated that the blood or other cell oxygen and signaling materials, which will be referred to herein as "BOX," is also an indicator of the adaptive ability of the immune system. As used herein, "BOX" is a measurement of blood cellular oxidative consumption capability, that is, the rate at which oxygen, NO, or other signaling materials, is consumed, including being bundled or packaged, which relates to the rate at which ROX is prepared for entry into the blood. Thus, BOX is also a measurement of a patient's adaptive immune system strength, or ability of blood cells to build capacity for signaling materials and to boost delivery of signaling materials for use by the body. By monitoring BOX levels, a patient's response to treatment over a longer period of time can be tracked. BOX also gives the dose at which the immune switch is triggered and can be of use in determining the proper dosage of medication.

People and animals who have an imbalance in the normal concentrations of ROX and BOX in blood (please see FIGS. 6 and 7), which are measurable, are believed to be more susceptible to disease and respond less effectively to immune system-boosting drugs such as Interferon. Thus, the accurate measurements of concentration of ROX and BOX may be of clinical and diagnostic value for diseases in animals and humans, in which the immune system and general health are of concern. As used herein, the term "imbalance" refers to a level of BOX, ROX, or generally signaling material that is either higher or lower than within a normal range based on a data obtained from individuals or other living organisms that are in a disease-free, relaxed or non-stressed and normal state. It is believed that a healthy living organism that is not undergoing an internal or external stress has a normal range of values for BOX and ROX.

It is further stated that an intensely high concentration of signaling materials, such as oxygen, for an exceptionally high duration of time, is also required by the body. This phenomenon is referred to as SOX, for a super-oxidative event. SOX may be generated by blood cells as well as other tissues, such as pancreatic islets. A typical SOX event is detectable upon a sharp increase in the level of signaling materials in a particular bodily fluid. For example, a SOX event may include a very large burst of NO, with an interval burst of $O_2$, accompanied by other strong indicators of the immune response, such as lactoferrin and myeloperoxidase. This scenario would be exceptionally effective in fighting cancer or AIDS or pathogens in the battle ground of the lymph nodes. If, by way of example, a SOX event could be triggered, the white blood cells associated with the bundling of signaling materials could be returned to the patient's own blood, bodily fluids or materials for use in actually combating a bodily disease or problem.

Additionally, the present invention contemplates a method for instigating or producing a SOX event in a fluid or material, which need not be bodily fluid or material possessed by the patient at issue. In the case that the bodily materials of a patient are too weak or generally incapable of producing a SOX event, a method of the present invention includes the steps of: 1) providing a suitable fluid or material that would be accepted by the immune system of a patient; 2) causing a SOX event; and 3) administering the SOX-capable material to the patient. This method would enable a patient to better withstand and overcome disease, drug therapy, or other stresses, based on that person's acquired ability to produce SOX events within the body.

Additionally, the measurement of the levels of signaling materials as compared to increasing amounts of blood, which is subjected to stress, provides information as to that blood's innate ability to overcome stress. This demonstration of strength in a person's blood, which is subjected to multiple, continuous stresses, is referred to herein as the blood's "turning point" or "turn around point."

Accordingly, the present method and apparatus measures the concentration of ROX and BOX in a sample of blood. When compared with an internal standard compound representing normal blood having normal concentrations of ROX and BOX, the present method and apparatus can also measure the toxicity of, and physiological response to drugs, chemicals, and other stresses. It may also be used as a research tool for those investigating biomarkers, or other phenomena. For example, T-lymphocytes may recruit and use ROX for oxidative attack, and normal cells may recruit and use ROX for glucose oxidation requirements. ROX is also helpful in explaining and giving an indication of Type II diabetic's resistance to insulin.

In the present method, blood is taken from a patient and compared to that of a healthy individual. The steps of the method include introducing a quantity of freshly drawn or frozen blood from a test individual or patient to a well in a testing apparatus having a reader connected to a sensor for detecting and measuring ROX, BOX, and SOX, as well as other information related to these events. An example of a testing apparatus suitable for this measurement is an Immunogram Analyzer™ (also referred to herein as "IA"). An Immunogram Analyzer™ generates an Immunogram™, which provides a data summary of a test run on the apparatus. An Immunogram™ can be used to identify non-responders for immune-boosting or modulating drugs, such as Interferon, treatment.

An Immunogram Analyzer™ is currently in clinical trials. In particular, clinical trials are under way with patients with Hepatitis C and a control group of healthy patients (University of Medicine & Dentistry of New Jersey IRB Protocol No. 0120090320). The purpose of the clinical trial is to identify patients who have an imbalance in the amount of ROX and BOX levels and examine their progress during the course of treatment with Interferon and ribavirin supplements. It is anticipated that measurement of ROX and BOX levels will have implications for the treatment of other chronic diseases, including diabetes and certain cancers.

The sensor of the testing apparatus detects the presence of ROX and BOX in the sample and generates an output of concentrations of ROX and BOX, including changes to these concentrations, over time. These output concentrations are thereafter compared to those for a healthy individual.

The testing apparatus may also be used during regular physical exams as a "baseline" indicator of homeostasis and health. For example, the effects of exercise, meditation, drugs, emotional and other stresses, etc., may be monitored for improving the body's condition or warning of potential weaknesses.

It is further stated that operating the testing apparatus as a closed system with chemical or other stress(es) yields instances lasting up to several hours of SOX.

With a simple blood test by the Immunogram™, one obtains the information required to make an informed recommendation for treatment. In an exemplary test, the steps include adding a sample of about 0.05-0.5 ml of patient blood to a well or cell. It is contemplated by the present invention that a suitable cell can be any structure, including the human skin, observed readings may be read through the skin without the necessity of taking a blood sample. ROX and BOX numbers can be computed and output by a reader/processor calibrated at zero and 100% based on the equivalent $O_2$ percent saturation. Up and down fluctuations, slopes of reaction rates, and ranges of values, are readable and of potential value.

An imbalance in the concentrations of ROX and BOX indicate a depressed immune system and one that is less responsive to treatment with immune-boosting or -modulating drugs. In some diseases, however, ROX and BOX may rise temporarily. Monitoring the levels of ROX and BOX for the same patient over a period of time may also be of clinical and diagnostic value. Accordingly, the present method, which measures the levels the ROX and BOX in blood, can be a tool for patient monitoring, drug screening, biomarker evaluation, as well as other related purposes.

Stressing the blood, by itself, or while measuring for ROX, BOX, and SOX, and subsequently using that blood or substances from that blood, to effect a cure for the patient, is an ultimate application of this technology.

Using this method to synthesize features of ROX, BOX, SOX, and other such events for the purposes of delivering drugs, therapy, cures, or protocols is an added application of this technology.

In particular, the invention will be described with reference to FIG. 1 wherein a biological system is represented schematically. In FIG. 1, the biological system, 100, includes a matrix, 102, which is capable of reversibly solvating signaling materials, 108. A transport material, 104, such as a white blood cell, extracts and/or bundles signaling materials, 108', in the matrix for transport to or use in addressing an undesirable component, 106, such as an infection, cancerous region, etc. for disposal thereof. For the purposes of the invention, the available quantity of signaling materials in the matrix, 102, is referred to as ROX and the quantity of signaling materials capable of being extracted by the bundling and/or transport material for consumption in disposal of an undesirable component is BOX. As would be realized ROX and BOX are both desired to be within a normal range, as this would suggest a sufficient quantity of signaling materials and a sufficient capability of utilization of the signaling materials.

The present invention further includes an apparatus for measuring ROX, BOX, SOX and other components that are relevant to an individual's immune system or other bodily functions. In particular, the present invention includes a testing apparatus capable of performing tests, which are useful research tools beyond the specific applications described herein.

The present invention can also apply to the nervous system, detoxification system, muscular system or energy system of a person or any bodily fluid including bundling capabilities such as white blood cells, so as to provide information about the strength and effectiveness of those systems to overcome stress depending on the individual's circumstances.

In one embodiment, the present method includes the steps of measuring the concentrations of ROX and BOX in a sample of blood in comparison to a norm. It is believed that the ROX and BOX concentrations found in blood are indicators for measuring the ability of an immune system to supply oxygen to defend against pathogens, to signal and coordinate the immune response, and to upkeep the level of homeostasis. The ROX and BOX of blood play an integral role in the mechanism used by the body of a human or animal to deliver large amounts of oxygen to tissues as required depending on the stress being placed on the body.

Thus the present invention can be used for a number of purposes relating to the immune response of humans and animals to a stress. For example, a method of the invention may be used to assess the health of people and animals generally, such as during a routine physical examination, and to assess the readiness of patients suffering from cancer, diabetes and auto-immune deficiency syndrome (AIDS) for immunotherapy regimens. The present method may further be used to assess the performance of athletes in improving their conditioning, and for testing people exposed to pollution and other external stresses. The present method may be employed to study diseases that are presently not well defined, such as fibromyalgia, neuromuscular and neurodegenerative diseases.

The present method may be used to more quickly and inexpensively prescreen new drugs for toxicity and immunogenicity, and to monitor individuals participating in clinical trials. Other chemicals, environmental contaminants, or physical stresses such as temperature and pressure, emotional stress, and so on, may also thus be tested.

A physician or veterinarian may use ROX and BOX as a measure of homeostasis. Next, he or she could use ROX and BOX to monitor a patient that may be sensitive to certain drugs and/or medical protocols. This may be done in at least two ways: by monitoring the patient by drawing blood for ROX and BOX measurements in real time as the drug or protocol is being administered, or by measuring the ROX and BOX of the patient's blood sample, which has been exposed to a drug or protocol, without actually exposing the patient to a potentially risky drug or protocol.

Another feature of the present invention includes a direct measurement of NO in the body. Prior to this invention, a direct measurement of NO has not been available. A demonstration of how this invention may be used in cancer prevention, prognosis, and cure, and as a research tool in clarifying major questions in cancer research is presented here.

Nitric oxide has been found to be very critical in the defense against cancer. In order for the body to make nitric oxide, the following steps must occur: 1) a gene must code an enzyme, nitric oxide synthase (NOS); 2) this code must be expressed; 3) the enzyme, NOS, must be manufactured from the NOS code; 4) the enzyme must have all the substrates and cofactors it needs to make nitric oxide; 5) the enzyme must be activated; and, relevant to this discovery, 6) the NO must be bundled in a form that is readily transported to and focused at the site of use.

The number of forms of NOS-coded genes is in the hundreds. These forms have been characterized as: endothelial, eNOS; inducible, iNOS; neural, nNOS; and mitochondrial, mNOS. This invention unveils a new type of NOS from blood—bNOS.

It is the end product, NO, that is most critical. Therefore, this discussion will use the simplified term, "NOS," for all of these categories.

In a literature review article entitled, An emerging role for endothelial nitric oxide synthase in chronic inflammation and cancer, Cancer Res. 2007 Feb. 15, 67(4):1407-10, L. Ying and L. J. Hofseth summarize that NOS modulates all critical cancer pathways including apoptosis, angiogenesis, cell cycle, invasion, and metastasis. These researchers point out that NOS is dysregulated in solid human tumors as well, and that NOS also has a role in chronic inflammation. Their recommendation is that NOS be used as a parameter in cancer prevention and treatment.

In a study of human liver tissue sections from 100 patients by M A Rahman et al. entitled, Co-expression of inducible nitric oxide synthase and cyclooxygenase-2 in hepatocellular carcinoma and surrounding liver: possible involvement of COX-2 in the angiogenesis of hepatitis C-virus positive cases *Clin Cancer Res* 2001 May; 7(5):1325-32, Rahman and coworkers conclude that while NOS expression alone is not a predictor of mortality in hepatitis C virus-positive (HCV) hepatocellular cancer (HCC) patients, the combination of NOS and COX-2 expression does correlate with mortality in HCV/HCC patients.

Recently, S Fujita et al., in an article entitled Genetic polymorphisms in the endothelial nitric oxide gene correlate with overall survival in advanced non-small-cell lung cancer patients treated with platinum-based doublet chemotherapy, *BMC Medical Genetics* 2010, 11:167, point out that there are over 160 genetic polymorphisms for NOS. They have discovered one special allele of the NOS gene that is a marker for survival in non-small-cell lung cancer (NSCLC) patients. In a study of 108 patients with NSCLC and on platinum-based treatment, this NOS gene is a marker for survival.

On the one hand, HCV patients with HCC do not survive when NOS and COX-2 genes are expressed. On the other hand, NSCLC patients expressing NOS do survive when a NOS gene is expressed. How can this apparent inconsistency be explained?

Genetic expression of NOS is a complex, costly and time-consuming method of analysis. More importantly, simple expression of the NOS gene is not a sufficient determination that NO is indeed formed. This invention provides a tool, the IA, which readily analyzes for available NO. Additionally, it allows us to postulate a mechanism that explains the apparent inconsistency. For example, one may predict that the NSCLC patients that survive do have the ROXNO mechanism, while the HVC/HCC patients that do not survive do not have adequate ROXNO, and that COX-2 requires oxygen and therefore is an additional burden for ROX.

The ability to form explanatory disease models for testing is critical in the quest for cancer cures. As used herein, an explanatory disease model is formed by the following steps: 1) create a disease model; 2) perform a clinical or research study to verify the model; 3) if the model is correct, expand upon it; and 4) if the model is incorrect, modify or improve it according to the data.

Figure 2:
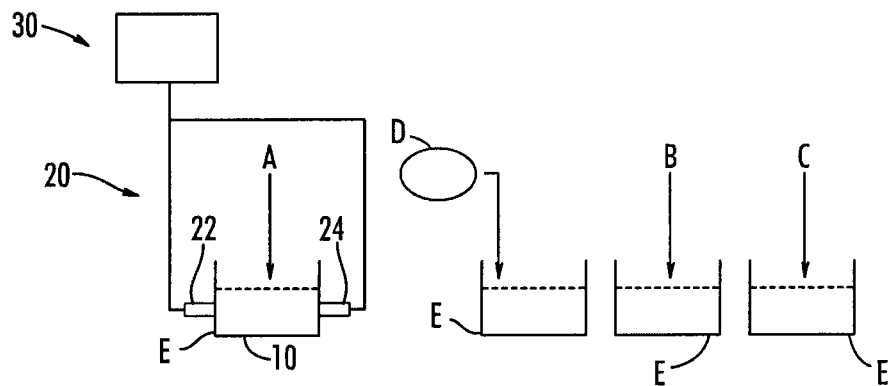
FIG. 2 is a schematic diagram illustrating the steps of a method for measuring concentrations of ROX and BOX in the blood sample of a patient being monitored according to one embodiment of the present invention.

As illustrated in FIG. 2, one embodiment of the present invention includes the following apparatus and method steps. First, a testing apparatus having a sample well 10 or cell with a sensor or probe 20 and a reader/processor 30 is provided. Significantly, the cell 10 can be any type of structure, including the human skin. The testing probes are inserted into the cell and the testing apparatus is calibrated so that the reading for levels of signaling materials is at zero. For example, a compound A, such as signaling material-free saline solution can be added to cell E derive an instrument baseline reading free of signaling material. Alternatively, a gas that is free of signaling material can be bubbled into the cell.

Once a baseline showing a zero reading for signaling materials is established, an amount of blood D is added to cell E. This amount of blood D can be a small quantity, such as between about 0.02 mL and about 0.10 mL, of freshly drawn or frozen blood from a test individual or patient. For convenience, a 3.00 mL sample of anticoagulated blood may be frozen for later analysis. Very small samples of blood, such as less than about 0.02 mL, may also be analyzed.

An initial reading is made of the levels of signaling materials in the sample prior to any stress being imposed. The mixture of compound A and blood D is then exposed to an initial stress B. A suitable stress would be physical shear stress produced by the administering syringe and/or a rotating magnetic stirrer. The sensor within the cell E then determines a drop in concentration of signaling materials, which is presumably brought on by the addition of stress B. Generally, this drop in signaling materials concentration yields the value of BOX, which is correlated to the ability of the system to incorporate signaling materials for transport. Following this drop, any rise in concentration of signaling materials yields the value of ROX, which correlates to the capacity of the system to provide a reservoir of signaling materials.

The sensor of the testing apparatus preferably includes two or more sensors—one may be a membrane-based oxygen electrode 22, such as a polarographic Clark oxygen electrode, which measures $O_2$, NO, $H_2S$ and other signaling materials that are unbound and can thus permeate through the membrane. In polarographic sensors, an anode, which is polarized, and a cathode are immersed in an electrolyte, into which oxygen and other signaling materials, permeates through the membrane. The anode/cathode pair causes current to flow in direct proportion to the amount of signaling material, such as oxygen, entering the system. The magnitude of the current thus directly correlates to the amount of signaling material entering the probe or sensor. It would be apparent that a membrane-based sensor necessarily depletes the sample of the material being tested as a result of consumption, yet the level of material consumed by the sensor is considered herein to be of an order of magnitude as to be insignificant for practical purposes.

The other sensor 24 or probe may be an optical fluorescence dissolved oxygen analyzer, such as an Ocean Optics ruthenium-coated fiber optical light emitting diode (LED) probe, and can also include other suitable light based devices, including a laser (hereinafter referred to collectively as an "optical sensor"), which determines an amount of value for $O_2$ and the bundled $O_2$ reservoir ($ROXO_2$). Other sensors, such as chip-based sensors, may also be used on the basis of price, convenience, and sensitivity to new signaling and reactive substances.

The testing apparatus of the present invention can include a computerized system, in which data lines from each probe are connected to a computer, which includes a processor, display and operating software to enable the processing and organizing of the data obtained by the probes, as well as the calculating of values for relevant events, such as a ROX, BOX, or SOX event.

As used herein, "$ROXO_2$" is determinable $O_2$ reservoir, and "ROXNO" is determinable NO reservoir. When bundled by the blood, and, in particular, the white blood cells, which are preparing signaling materials for use by the body, $ROXO_2$ and ROXNO are unable to travel through the membrane sensor. However, after a BOX event occurs, increased levels of signaling materials in the sample, as determined by either the membrane or optical sensor, which tend to track each other, yield amounts of $ROXO_2$ and ROXNO. For example, if a reading from the membrane sensor goes to zero, meaning all unbound $O_2$ has been measured or has permeated through the membrane, a subsequent rise in the reading from the optical sensor can be considered an alternative determination of the amount of $ROXO_2$. Similarly, once a membrane reading for NO goes to zero, meaning all unbound NO has been measured or has permeated through the membrane, a subsequent rise in the reading from the membrane sensor of this signaling material yields an amount of ROXNO assuming any oxygen is accounted for separately such as by an optical sensor.

Figure 6:
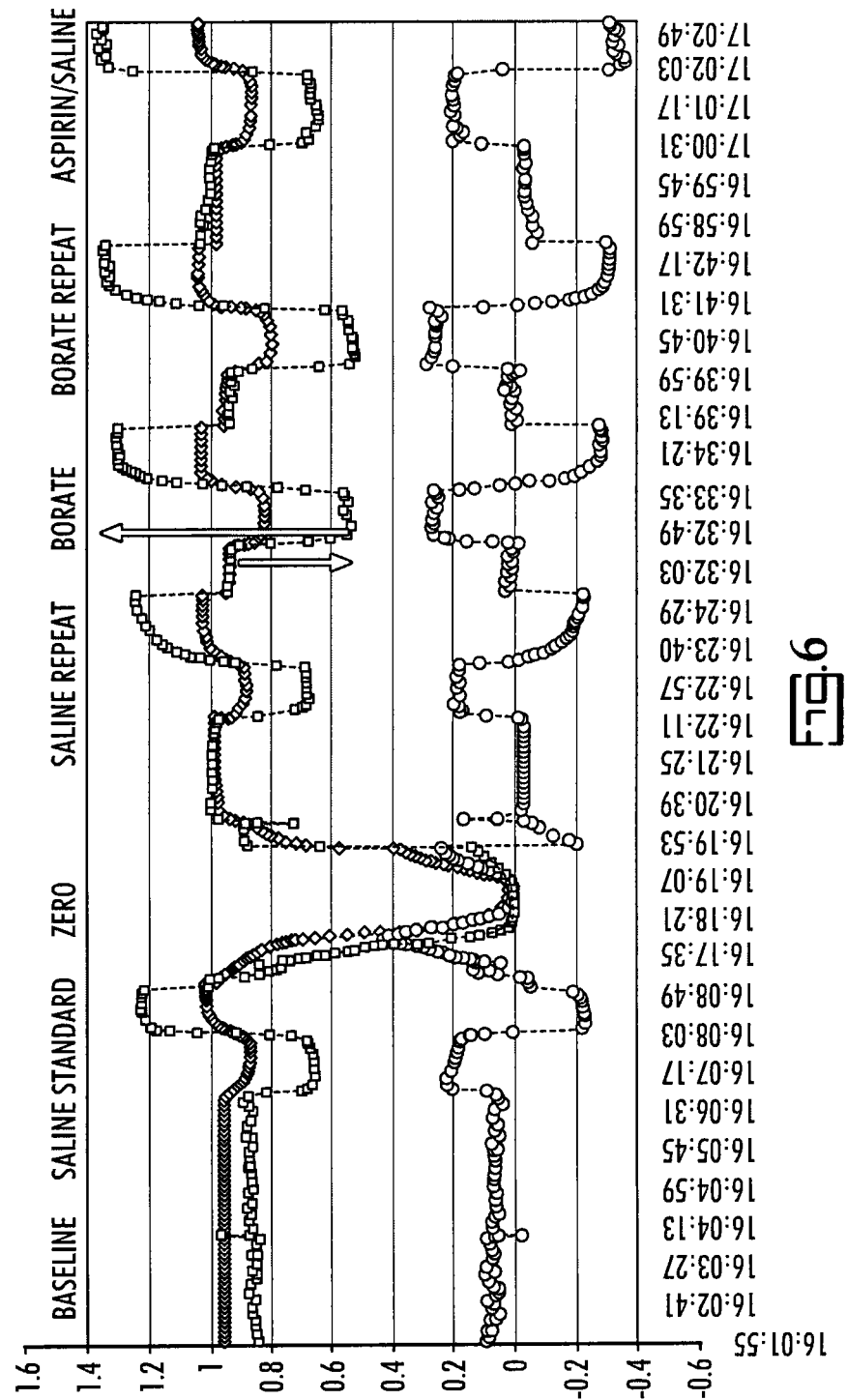
FIG. 6 is a graph showing a typical series of runs on a testing apparatus according to one embodiment of the present invention.
Figure 7:
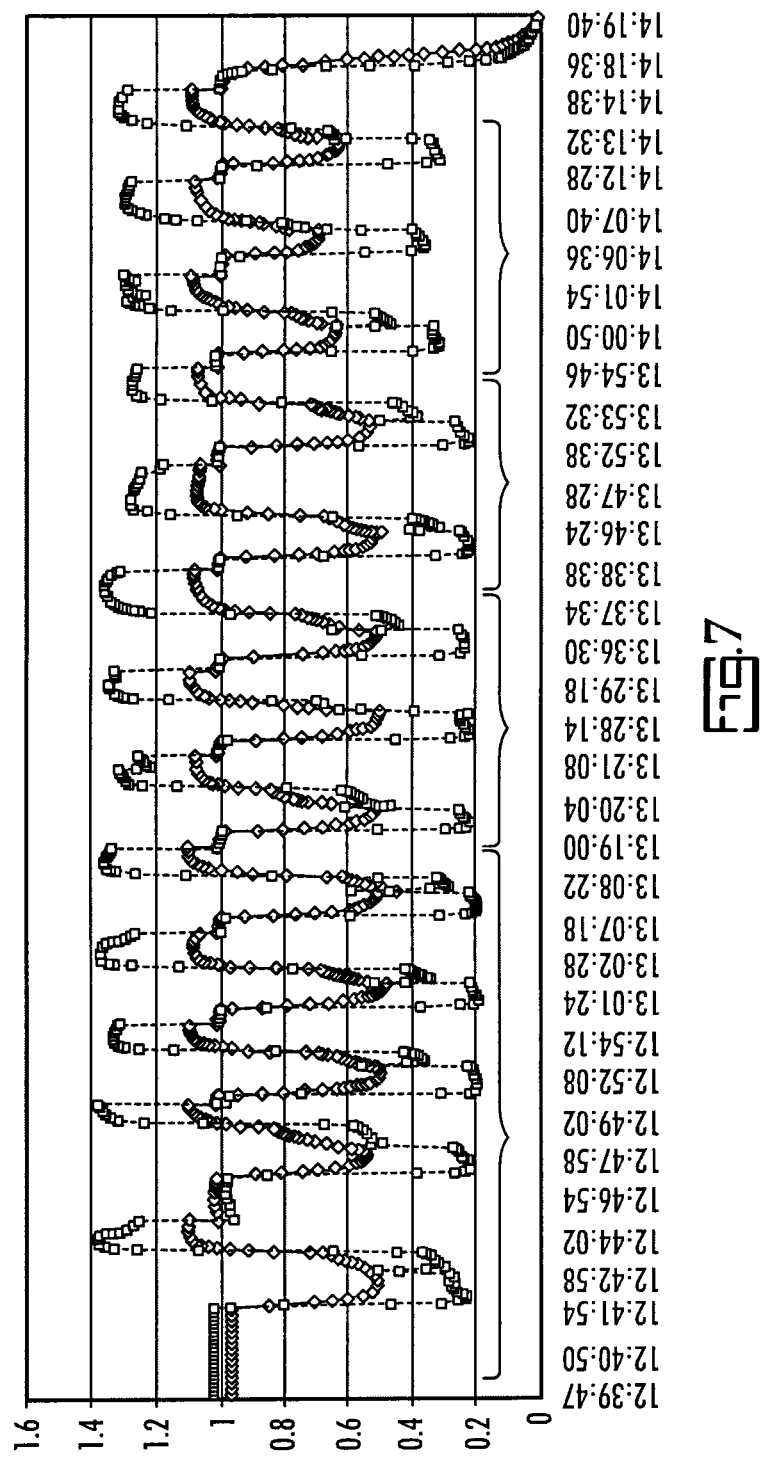
FIG. 7 is a graph indicating a second series of runs to establish reproducibility of the testing apparatus, and to demonstrate toxicity of ACD (acid-citrate-dextrose) anticoagulant according to one embodiment of the present invention.

Between these two or more sensors, therefore, the testing provides a reading for $O_2$, NO, $ROXO_2$, and NO that is in a bundled reservoir (ROXNO), as shown in FIGS. 6 and 7. For this embodiment, a complete ROX measurement includes $ROXO_2$+ROXNO. Thus, the readings from the membrane probe and the optical probe together provide a total concentration of BOX and ROX ($ROXO_2$+ROXNO) in the sample after exposure to physical stress B. Also, the slopes of the curves in FIGS. 6 and 7 yield valuable information with respect to the rates of reaction of these components. For example, a rise in levels of signaling materials can indicate a ROX event and its timing, whereas a drop in the level of signaling materials can indicate a BOX event and its timing.

In summary, when signaling materials are being used in reaction to a stress, levels of signaling materials will be shown to drop. However, once these drops occur, any subsequent rises in the levels of signaling materials indicate the presence and amounts of bundled signaling materials, or reservoirs of signaling materials, which were previously undetected.

As further illustrated in FIG. 2, the mixture of compound A and blood D is next exposed to a chemical stress C. Stress C may be a powerful chemical such as 6% aqueous phenol or other type of stress strong enough to release essentially any remaining ROX in the sample. The sensor within cell E then measures any rise in oxygen and NO, which is presumably a result of the introduction of stress C. This rise in oxygen and NO after this stress is applied yields the amount of remaining ROX in the solution. The levels of signaling materials such as these within the sample over time are tracked and recorded by the reader/processor 30 of the testing apparatus.

Importantly, the BOX and ROX of a bodily fluid appear to affect one another. For example, if a bodily fluid has an abnormally low ROX, the BOX for that same fluid will also tend to be low, as there is less available signaling material to bundle. Similarly, if the BOX of a bodily fluid is abnormally low, in that the fluid has less bundling capabilities, the ROX will tend to be low, as there will be less bundled signaling material. Moreover, the innate strength of a bodily fluid can be determined by the detectable ROX and BOX events of that fluid over time. In a stronger than normal fluid, the addition of more stresses and/or stronger stresses would yield a value for BOX and/or ROX within a normal range, as compared with a weaker than normal fluid, which would yield values for BOX and/or ROX outside of the normal range if subjected to the same stresses.

Changes in concentrations of ROX and BOX can further indicate whether a person's response to stress is acute or chronic. For example, substantially weakened BOX may be a predictor for an acute versus chronic response. If the BOX of a patient is abnormally low after a stressful event, the patient's response could be a chronic response, whereas if the BOX level is normal and higher after stress, this could be an indication of an acute response.

Figure 3:
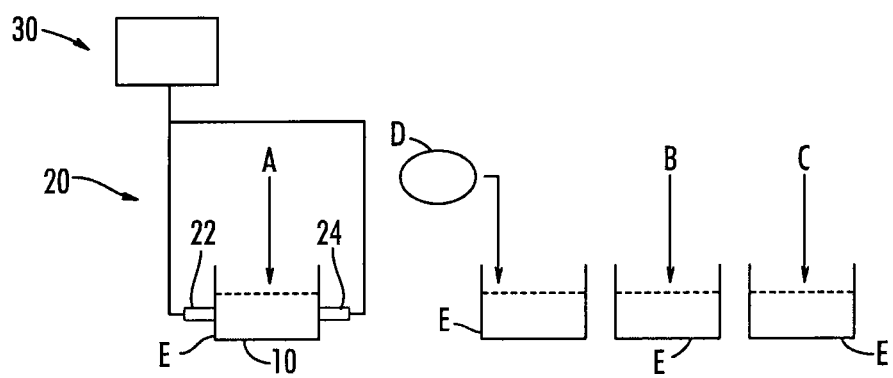
FIG. 3 is a schematic diagram illustrating the steps of a method for predicting the toxicity of a given drug or other stress according to one embodiment of the present invention

The present invention further includes a method for measuring the toxicity of a given drug or other stress. This method is different from the method in FIG. 2 because an internal standard (or the patient's blood), in conjunction with a given drug or toxin, may be used to determine that drug's toxicity with respect to a standard, or the individual patient's sensitivity to that drug or toxin. As shown in FIG. 3, the testing apparatus having a sample well 10 or cell with a sensor 20 and a reader/processor 30 is provided. A compound A is introduced into a cell E of the testing apparatus. Compound D, which is a surrogate blood sample such as anti-coagulated bovine blood, is next added to the cell E. The mixture of compound A and compound D is then exposed to a first chemical stress B. The sensor of cell E measures any drop in signaling materials, which generates the amount of BOX in the sample. Next, a second chemical stress C is added to the mixture in the cell E. The measured rise in signaling materials as detected by the sensor yields the amount of ROX in the sample. Thus the toxicity of a given drug may be tested, either for general drug screening, or for monitoring drug toxicity for a given patient.

Figure 4:
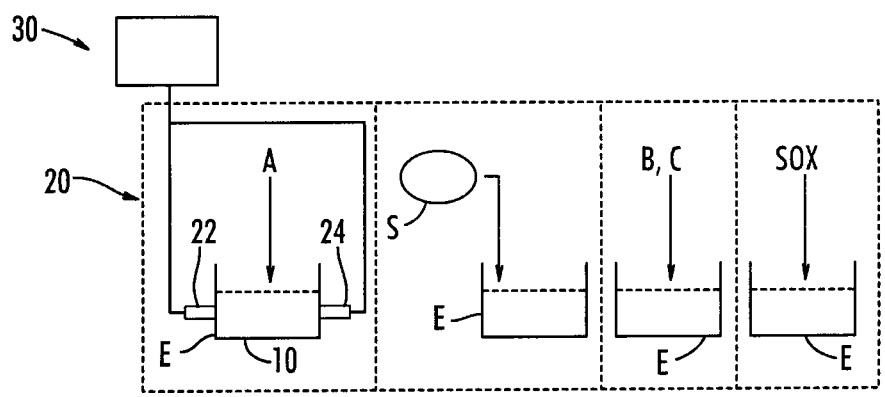
FIG. 4 illustrates one possibility for obtaining a SOX event through steps of a method according to one embodiment of the present invention.

The present invention further includes a method for obtaining a SOX event and for measuring the ROX and BOX of a patient undergoing such an event. As illustrated in FIG. 4, a compound A is added to a cell E which has a sensor or sensors. A blood sample S is added to the cell. A physical or chemical stress B is added. The drop in signaling materials measured by the cell yields BOX. A physical or chemical stress C and others may be added to boost the 'firing' of the immune response, and the cell is closed to the outside environment. A SOX event takes place over time and is recorded. SOX represents an actual 'firing' of the blood cells. Hence, the mixture containing this material may be of utmost use, for example in cancer and AIDS therapy and/or cure, when returned to the patient.

To be of clinical and diagnostic value, the concentration readings of ROX and BOX are compared to those for healthy individuals, or to the same individual during a normal state of health. Generally, if the concentrations of ROX and BOX for the test individual or patient are outside of a normal range as compared to the concentrations for those of the healthy individual (or of the same patient, during a healthy period), the test individual or patient has an imbalance, and thus a likely lower ability to respond to attack by disease or a reduced response to immunomodulators than the average person. If the test individual's or patient's concentrations of ROX or BOX are within the normal range of concentrations as compared to those of the healthy individual, the test individual would be expected to respond normally to disease and the patient should respond well to immunomodulation.

As will be appreciated here, the membrane-based sensor and optical sensor, if employed, both provide a measurement that correlates to molecular oxygen, however, the membrane-based sensor detects other materials, such as NO. In a preferred embodiment, the correlation of the measurements provides an analytical tool which allows for the indirect determination of additional components thereby greatly extending the diagnostic and biological information.

Figure 5:
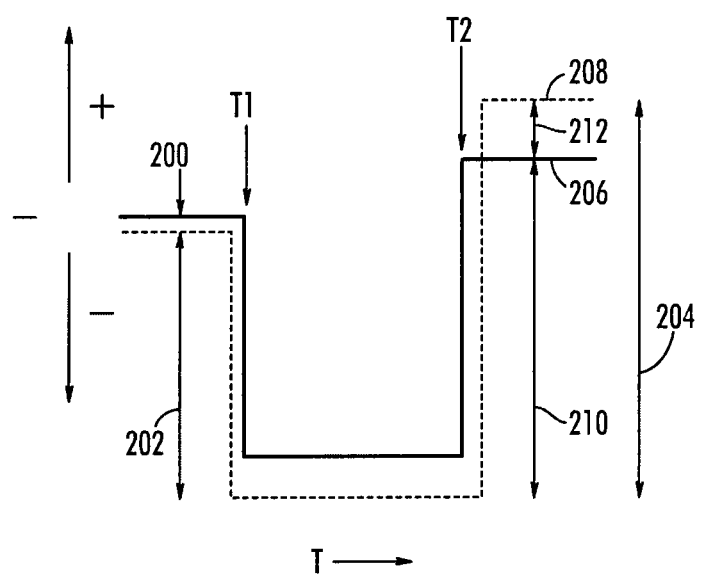
FIG. 5. is a schematic representation of an Immunogram™ according to one embodiment of the present invention.

A schematic Immunogram™ is provided in FIG. 5. In the Immunogram, the results of the optical measurement are indicated as a function of time (T) by the solid line and the results of the membrane-based sensor are indicated by the dashed line. A signal moving upward indicates an increase in measured materials and a signal moving downward indicates a decrease in measured material.

With reference to FIG. 5, a baseline, 200, is established which is representative of the total amount of signaling materials measured in the matrix. The two signals are typically similar with the exception of a high level of NO or other materials which are measured by the membrane-based sensor. At a specific time, T1, a stress is applied to the system whereby signaling materials are extracted from the matrix by the white blood cells, for example, for transport. The decrease in measured signaling material, 202, correlates to the signaling material removed from the matrix for transport which is referred to herein as BOX. At time, T2, stress is increased, and this additional stress causes release of signaling materials to the matrix. The total amount of signaling materials, 204, is ROX. The amount of oxygen as measured by the optical sensor, 206, allows for a determination of the signaling materials which are not oxygen, such as nitrous oxide by the difference between the signaling material measured by the membrane-based sensor, 208, and that measured by the optical sensor, 206, which is referred to as ROXNO, 212. In particular, after ROX is formed, and ROX is greater as determined by the membrane sensor than the optical sensor, the difference is the amount of NO. $ROXO_2$, indicated by 210, is the sum total of ROX less the ROXNO, indicated by 212.

An example of data generated from a testing apparatus of the present invention is shown in FIG. 6. Six runs are shown in this figure. Starting from the left of the diagram, the first and third runs are repetitions with saline. The second run is a zero calibration where helium bubbling (or any other procedure) is used to mark a 'zero' point, with 20.9% atmospheric oxygen equilibration used to determine the baseline. The next two runs are repeat injections with a saline/borate mixture, demonstrating the increases of BOX and ROX in the presence of borate as used typically in ocular washes. The final run demonstrates the effect of aspirin, indicating very rapid releases of NO as expected from the vasodilating and blood-thinning properties of aspirin. The run also demonstrates a new pathway for the mechanism of activity of aspirin in blood: this pathway affects blood directly and instantly. The new pathway could also help to discover the pathway and effect of other drugs.

As further shown, the output of a Clark type sensor with a membrane, which measures $O_2$ and NO, is represented by short dashes with open squares. The optical sensor (shown by solid line with diamonds) measures only $O_2$. The difference between the two sensors (large dashes with open circles) is shown for convenience. The drop in both sensors is due to the addition of blood. The drop in the membrane sensor line is defined as BOX, and is indicated by the smaller arrow in FIG. 6. The optical sensor curve does not drop as much as the membrane sensor. The difference, open circles, represents oxygen which cannot cross the membrane but can be read optically. This is $ROXO_2$. The point at which Stress C is added represents a large increase in readings. The larger arrow in FIG. 6 indicates the rise, which is defined as ROX. Note that the membrane reading is higher than the optical reading. This means that NO (and possibly other compounds such as $H_2S$) have been newly released. This is due to the rupture of ROXNO plus any instantly manufactured NO. The present invention provides the only known method for directly determining NO present in a fluid or material. Furthermore, if the material being tested initially shows a zero concentration for NO, and NO is thereafter detected, the discovery of bNOS is further shown in such a test run. Other sensors, with or without membranes may also be used, individually or in combination.

Table I, as shown below, summarizes the data from FIG. 6 and demonstrates the use of the present invention to determine the toxicity and other effects of pharmaceuticals on blood. Both borate eye wash and aspirin affect ROX and BOX, when compared to saline runs on a patient's blood. The effect of aspirin on the same patient's indicates anticlotting results for this patient. The rapid rise of NO formation from ROXNO and resultant NO synthesis, not shown in the table, is valuable, for example, in the analysis of aspirin in blood. In FIG. 6, a large amount of NO is formed in the interval between the markers, 2 seconds apart.

TABLE I

Summary of FIG. 6, demonstrating apparatus use. Effect of borate and aspirin on human blood aged for 5 days at room temperature. 0.10 ml blood, 0.9 ml saline. Numbers are in percent of air saturation. Comments are subject to researcher interpretation.

|  | 1<br>Saline<br>Avg of 2 runs | 2<br>Borate<br>Avg of 2 runs | 3<br>Aspirin | Comments |
|---|---|---|---|---|
| BOX | 27 | 41 | 35 | Aspirin and borate increase |
| ROX | 57 | 79 | 74 | ROX and BOX, with borate |
| $ROXO_2$ | 20 | 27 | 29 | having a stronger influence |
| ROXNO | 23 | 31 | 34 | than aspirin. |
| Notes | basis | Borate is a booster at medical concentrations | Aspirin boosts $ROXO_2$ and ROXNO | Aspirin produces more $ROXO_2$ and ROXNO. Aspirin induces a measurable and rapid rise of NO, a 37% rise in 2 seconds (FIG. 4) |

A large amount of additional information may be gleaned from a typical test run by the testing apparatus: the BOX, indicated by a drop in the detected signaling materials, can yield a slope and concentration at several points, from which Michaelis-Menten kinetics (curve of oxygen as a function of reaction rate), and more sophisticated techniques for analyzing reaction kinetics, may be derived. The slow rise following, gives the rates of oxygen and NO rise, the ROX portion gives rates of NO and $O_2$ delivery. Furthermore, if it is understood that hemoglobin is present in a blood sample, the BOX curve at 50% saturation level in that sample should be showing a substantial decrease in the slope because rate of $O_2$ consumption. The slopes of BOX show that the mechanism for blood and $O_2$ consumption is beyond simple diffusion of $O_2$ out of hemoglobin. Electromagnetic forces are also at work. In particular, white blood cells are also grabbing or using signaling materials, which are presumably paramagnetic in nature when in bundled form, through the use of electromagnetic forces. Because below 50% hemoglobin begins to release additional $O_2$ into solution. If the $O_2$ consumption were constant, the slope would appear more shallow because new oxygen would be added.

FIG. 7 is a graph showing 12 runs with the testing apparatus. These runs were performed to test the reproducibility of the apparatus, the processing of the blood surrogate standard, and the skill of the operator in measuring blood standards. Starting from the left, the first 3 runs were done be Experimenter 1. The rest of the runs were performed by Experimenter 2. ACD anticoagulant concentrations were tested as well. The results show that freezing the blood standards reduces BOX and ROX slightly, and the higher concentrations of ACD, combined with freezing, reduces ROX and BOX the most indicating harsh treatment of the standard blood.

The results of the test of FIG. 7 are summarized below in Table II. These series of runs demonstrate how to determine the optimum operating concentrations and conditions of the testing apparatus, and how to use the apparatus to train operators of the apparatus.

TABLE II

Summary of FIG. 7, demonstrating apparatus use. Effect of freezing and high concentrations of ACD anticoagulant on bovine blood standard. 0.05 ml blood, 0.3 ml saline. Numbers are in percent of air saturation. Comments are subject to researcher interpretation.

|  | 1 Avg of 5 runs Fresh 1.2x ACD | 2 Avg of 3 runs Frozen 1.2x ACD | 3 Avg of 2 runs Fresh 2.2x ACD | 4 Avg of 3 runs Frozen 2.2x ACD | Comments |
|---|---|---|---|---|---|
| BOX | 78 | 79 | 80 | 74 | Stress is highest |
| ROX | 118 | 113 | 108 | 99 | with frozen 2.2 |
| ROXO$_2$ | 31 | 30 | 33 | 34 | ACD. |
| ROXNO | 26 | 25 | 20 | 21 | Blood cells make |
| Notes |  | Freezing 1.2x ACD Lowers ROX by 4% | | Freezing 2.2 ACD Lowers BOX by 8% Lowers ROX by 9% Increases ROXO$_2$ by 10% Lowers ROXNO by 25% | more ROXO$_2$ in anticipation of chemical toxicity. Toxicity prevents generation of ROXNO. |

Preferably for a clinical study, the normal concentrations of ROX and BOX by which to compare test samples will be obtained by sampling a large population of individuals who are not taking prescribed medications and who describe themselves as not being sick. A distribution of ROX and BOX concentrations will be generated from this population. The mean will define a baseline set to a standard number such as 100.

The Tables III and IV below show data collected from a private clinic relating to the response in blood samples of "normal" individuals (individuals that were disease free at the time of the test) as compared to individuals infected with Hepatitis C. As illustrated in Table III, a medium stress standard was established, and a series of runs were made to measure oxygen levels in the samples by a membrane sensor and an optical sensor. Based on these measurements, the membrane sensor detected a percentage of greater than about 20% of oxygen, and the optical sensor detected a percentage of greater than about 11.5% of oxygen in blood that was in a stressed state.

TABLE III

Private Clinic - Medium stress response

| RUN | DESCRIPTION | MEMBRANE O$_2$ + NO, % | OPTICAL O$_2$ + ROXO$_2$, % |
|---|---|---|---|
| 1 | MedX Stress Std | 34 | 7.8 |
| 2 | HepC | 26.4 | 12.4 |
| 3 | Normal | 13.1 | 11.1 |

TABLE III-continued

Private Clinic - Medium stress response

| RUN | DESCRIPTION | MEMBRANE O$_2$ + NO, % | OPTICAL O$_2$ + ROXO$_2$, % |
|---|---|---|---|
| 4 | HepC | 23.6 | 15.6 |
| 5 | Normal | 19.1 | 9.4 |
| 6 | Normal | 15.2 | 4.6 |

"Normal" Medium Stress
M < 20 L < 11.5

Table IV shows the ROX, BOX and level of NO detected on the blood samples from the same individuals. Based on the measurements of ROX, BOX and NO, the normal blood exhibited a ROX between about 40 and about 110, a BOX between about 40 and about 160, and NO of less than about 200. The purpose of this table is to show the method of determining the range of values of normal ROX and BOX for purposes of identifying an imbalance with respect to BOX and ROX. The actual numbers obtained are not as important as the fact that a range of BOX and ROX was determined to be normal within this sampling of individuals. In case of HepC patients, for example, the range of normalcy can be subsequently adjusted as more clinical data are obtained.

TABLE IV

Private Clinic - ROX, BOX, NO

| RUN | DESCRIPTION | ROX | BOX | NO |
|---|---|---|---|---|
| 1 | MedX Stress Std | 82.7 | 200 | 206 |
| 2 | HepC | 110.6 | 187 | 237 |
| 3 | Normal | 108.3 | 155 | 162 |
| 4 | HepC | 113.9 | 173 | 205 |
| 5 | Normal | 101.1 | 101 | 93 |
| 6 | Normal | 91.1 | 44 | 45 |

"Normal" ROX: 40 < ROX < 110
"Normal" BOX: 40 < BOX < 160
"Normal" NO: NO < 200

Table V below provides information relating to the blood turning point in relation to the present invention. Tests are run with gradual increases in toxin, on increasing levels of blood. After the BOX reading at Stress 1, the chemical stress is added in portions, instead of being added at once. Typically, an amount of toxin, such as 0.2 ml of 6% phenol is added sequentially three times, for Stress 2, 3, and 4. At low levels of blood, ROX begins to form, and the $O_2$ and NO levels rise. Blood is overcome by toxin and $O_2$ and NO are released.

At high levels of blood, the blood is strong enough to overcome Stress 2, $O_2$ and NO levels do not rise, instead, more oxygen is consumed. This level is a turning point, signifying that the blood overcomes that stress.

For the optical probe above, the turning point begins at 0.10 ml of blood. For the membrane probe, the turning point begins at 0.20 ml of blood. A person with stronger blood would require less blood to reach the turning point. In this way, a profile of immune system strength may be monitored for every individual. Each individual may thus optimize their state of health by observing two separate profiles (optical and membrane profiles) as a function of habits, exercise, exposure to drugs and toxins, etc.

TABLE V

Determination of immune system strength.

| | | Stress Level Low = 1 High = 4 | | | |
| --- | --- | --- | --- | --- | --- |
| | | 1 | 2 | 3 | 4 |
| Optical Probe | 0.02 ml blood | Weak | Weak | Weak | Weak |
| Turning Point | 0.05 ml blood | Weak | Weak | Weak | Weak |
| Weak or Strong | 0.10 ml blood | Weak | Weak | Strong | Strong |
| | 0.20 ml blood | Weak | Weak | Strong | Strong |
| Membrane Probe | 0.02 ml blood | Weak | Weak | Weak | Weak |
| Turning Point | 0.05 ml blood | Weak | Weak | Weak | Weak |
| Weak or Strong | 0.10 ml blood | Weak | Weak | Weak | Strong |
| | 0.20 ml blood | Weak | Weak | Strong | Strong |

Figure 8:
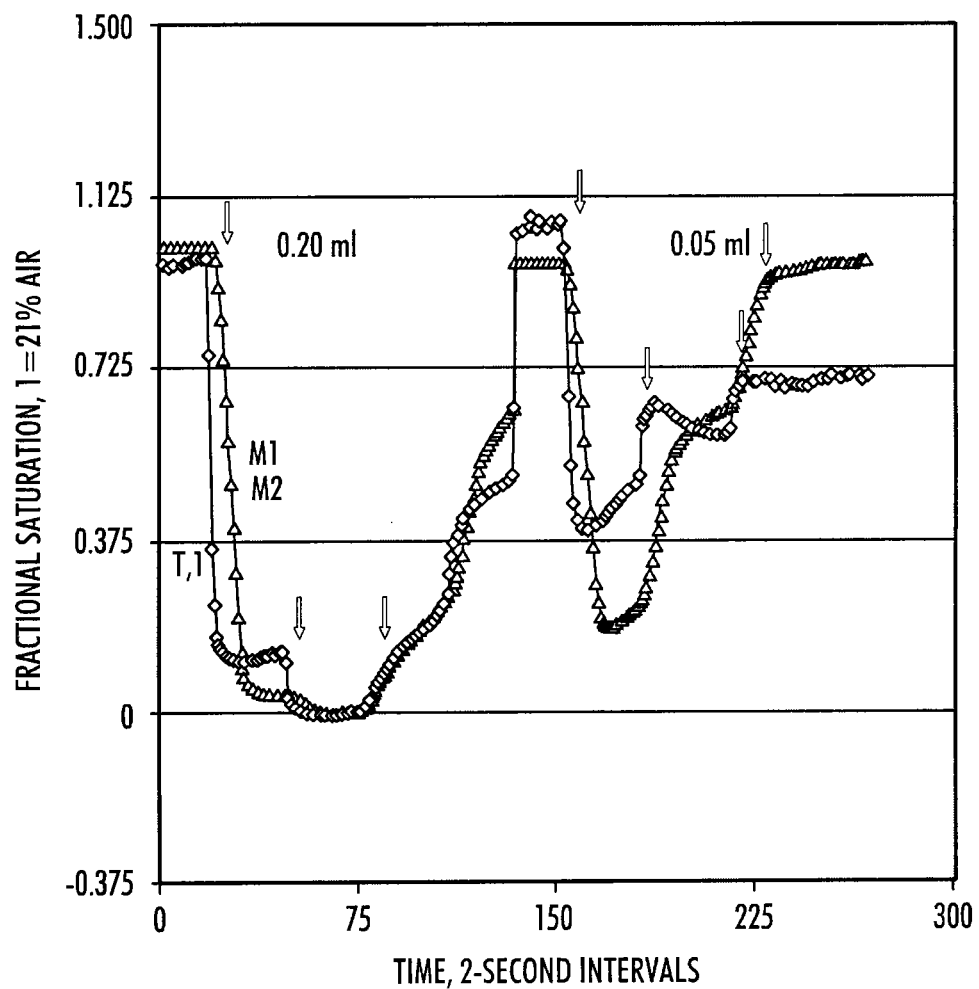
FIG. 8 is a graph showing two runs indicating a maximum BOX rate and turning point data determined by a testing apparatus according to one embodiment of the present invention.

FIG. 8 is a graph showing two tests. The result of these tests are detailed in Table VI. Numbers presented are in percent saturation (100%=amount of equivalent oxygen in water, equilibrated with air at atmospheric pressure and 25° C.). Runs for 0.20 and 0.05 ml blood are shown in FIG. 8. Maximum BOX rates are from shear stress only. NO formation is after chemical stress is added and the runs are completed.

These data may be used in many ways to evaluate the overall strength of the immune system. For example, maximum BOX rate profiles for both probes may be observed for a patient on a given medicine, and compared to a previous run without the medicine, to evaluate the patient's response to the drug. This may also be done to evaluate an athlete's response to a workout regimen, etc.

The 'turn around' point may be located from the runs and used to calibrate a subject's general immune strength, much like a titration of blood, as shown in FIG. 8.

Final NO concentration, and overall NO generation, indicate very important aspects of blood thinning for heart patients, NO availability and ROXNO dosage for neuromuscular degeneration patients, especially Duchenne's Muscular Dystrophy patients, that are known to have an NO imbalance.

TABLE VI

Determination of immune system strength by measurement of Maximum BOX rate, and total NO formed.

| | Maximum BOX rate total/per ml blood Optical Probe | Maximum BOX rate total/per ml blood Membrane Probe | NO Formation total/per ml blood |
| --- | --- | --- | --- |
| 0.02 ml blood | 8.47/423.5 | 4.24/212 | 39.33/1,966.5 |
| 0.05 ml blood | 32.98/659.6 | 7.87/157.4 | 39.33/786.6 |

TABLE VI-continued

Determination of immune system strength by measurement of Maximum BOX rate, and total NO formed.

| | Maximum BOX rate total/per ml blood Optical Probe | Maximum BOX rate total/per ml blood Membrane Probe | NO Formation total/per ml blood |
| --- | --- | --- | --- |
| 0.10 ml blood | 37.52/375.2 | 9.08/90.8 | 35.55/355.5 |
| 0.20 ml blood | 42.36/211.8 | 17.4/87 | 29.95/149.75 |

It is further contemplated by the present invention that the determination of ROX and BOX can be utilized in numerous applications from enhancing the ability of a living organism to combat disease, accept a therapy, including an organ transplant, and generally improve health.

Thus, the present invention further includes a method for controlling the concentrations of ROX and BOX, comprising the steps of: 1) providing a sensor; 2) providing a sample or organism including an amount of bodily material with an amount of signaling material; 3) determining a baseline value by the sensor for the amount of signaling material; 4) introducing a stress into the sample or organism; 5) determining by the sensor a value for ROX in the sample or organism; 6) determining by the sensor a value for BOX in the sample or organism; and introducing a controlling or blocking material into the sample or organism, wherein the controlling material is capable of altering either the value for ROX or BOX in the sample or organism. Based on this method, a successful controlling or blocking material can be identified and administered to a living organism in an effective amount to adjust any imbalance of ROX and BOX, to create a SOX event, or prepare the organism for imminent stress.

The present invention further includes a method for predicting the onset of rejection to an organ transplant or to a drug, comprising the steps of: 1) providing a sensor; 2) providing a sample from a patient intending to undergo treatment, including an amount of bodily material with an amount of signaling material; 3) determining by the sensor a baseline value for the amount of signaling material; 4) introducing a stress into the sample, wherein the stress includes an amount of treatment material, and wherein the treatment material is a material that is integral to the treatment, namely an organ transplant; 5) determining by the sensor a value for ROX in the sample; and 6) determining by the sensor a value for BOX in said sample. Based on the ROX and BOX values for the patient subjected to a sampling of the impending treatment, a patient's ability to accept a new organ or the rejection of an existing transplant can be determined.

Those familiar with life science research will appreciate that many modifications and substitutions can be made to the foregoing preferred embodiments of the present invention without departing from the spirit and scope of the present invention, defined by the appended claims.

What is claimed is:

1. A method for determining ROX and BOX, comprising the steps of:
   providing a first sensor and a second sensor;
   providing a sample including an amount of bodily material, said sample including molecular oxygen and nitric oxide, wherein said first sensor is adapted to sense said molecular oxygen and to send a signal related to the amount of said molecular oxygen, and wherein said second sensor is adapted to sense said molecular oxygen and said nitric oxide and to send a signal related to the amount of said molecular oxygen and said nitric oxide;

providing a processor in electrical connection with said first and second sensors and responsive to said signals received from said first and second sensors, and wherein said processor is adapted to determine the amount of said molecular oxygen and said nitric oxide from the difference between said first sensor signal and said second sensor signal;

sensing by said first sensor molecular oxygen and by said second sensor molecular oxygen and nitric oxide present in said sample;

then sending by said first and second sensors a first set of signals to said processor at a first point in time;

determining by said processor from said first set of signals baseline values for said molecular oxygen and nitric oxide;

introducing a first stress into said sample, wherein said first stress is a stress that is administered over time;

then sensing over time with said first and second sensors said molecular oxygen and said nitric oxide present in said stressed sample;

then sending by said first and second sensors a second set of signals to said processor at a second point in time;

then sending by said first and second sensors a third set of signals to said processor at third point in time;

determining by said processor from said second set of signals BOX values for said molecular oxygen and said nitric oxide, which are a measurement of a decrease in said molecular oxygen and said nitric oxide in said sample as compared to said baseline values; and determining by said processor from said third set of signals ROX values for said molecular oxygen and said nitric oxide, which are a measurement of an increase in said molecular oxygen and said nitric oxide in said sample as compared to said BOX values, respectively, wherein said increase in said nitric oxide is determined from the difference in said first sensor signal and said second sensor signal;

introducing a second stress into said stressed sample;

then sensing over time with said first and second sensors said molecular oxygen and said nitric oxygen;

then sending by said first and second sensors a fourth set of signals to said processor at a fourth point in time;

determining a SOX value, which is a sharp increase in either said molecular oxygen or said nitric oxide following said introduction of said second stress in said stressed sample as compared to said ROX value for said molecular oxygen and said nitric oxide, respectively; and administering said sample to a subject following said determination of said SOX value.

2. The method as recited in claim 1, wherein said first sensor is an optical probe and said second sensor is a membrane probe.

3. The method as recited in claim 1, further comprising the steps of providing a cell and introducing said sample into said cell.

4. The method as recited in claim 1, further comprising the step of determining a turning point for said amount of bodily material in said sample.

5. The method as recited in claim 1, wherein said bodily material is blood and wherein a higher optical probe signal of said third set of signals indicates said ROX value for said molecular oxygen, and wherein a membrane-based sensor signal of said third set of signals higher than said baseline value indicates a ROX value for said nitric oxide.

6. An apparatus for measuring ROX and BOX in a sample having an amount of molecular oxygen and nitric oxide and subjected to a stress source, comprising:

an optical probe and a membrane probe in a cell that are operatively connected to a processor, wherein said optical probe is adapted to detect unbound molecular oxygen, which is molecular oxygen that is not bound to hemoglobin or white blood cells, in a sample of bodily material contained in said cell, and to deliver a signal over time as to the amount of said unbound molecular oxygen from said sample to said processor through a first data line, wherein said membrane probe is adapted to detect unbound molecular oxygen and unbound nitric oxide, which is nitric oxide that is not bound to hemoglobin or white blood cells, in said sample of bodily material and to deliver signals over time as to the amount of said unbound molecular oxygen and unbound nitric oxide from said sample of bodily material to said processor through a second data line, wherein said processor is adapted to compute a BOX, ROX and SOX values for molecular oxygen and nitric oxide in said sample of bodily material, wherein said BOX value for each of said molecular oxygen and said nitric oxide is a measurement of the rate at which said unbound molecular oxygen and said unbound nitric oxide become bundled, that is attached to white blood cells and thus undetectable by said optical and membrane probes, respectively, based on a detected decrease in said unbound oxygen and said unbound nitric oxide over time when said sample is subjected to a stress by a stress source, wherein said ROX value for each said molecular oxygen and said nitric oxide is a measurement of the amount of bundled molecular oxygen and bundled nitric oxide, that is molecular oxygen and nitric oxide that were attached to white blood cells and thus undetectable by said optical and membrane probes, respectively, based on a detected increase in said unbound molecular oxygen and said unbound nitric oxide at any point in time after said BOX value is computed, wherein said processor computes said ROX value for said nitric oxide by determining the difference between said optical probe signal and said membrane probe signal, wherein said SOX value is a measurement of a sharp increase in said nitric oxide or said molecular oxygen as compared to said ROX value for nitric oxide and molecular oxygen at any point in time after said BOX value is computed, and wherein upon detection of said sharp increase, said bodily material is administered to a subject.

7. The apparatus as recited in claim 6, wherein said membrane probe is a polarographic oxygen electrode.

8. The apparatus as recited in claim 6, wherein said optical probe is a ruthenium-coated fiber optical light emitting diode probe.

9. The apparatus as recited in claim 6, wherein said stress source includes at least one full continuous stress, at least one partial stress, or at least one stress administered more than once over time.

10. The apparatus as recited in claim 6, wherein said stress source is a physical stress.

11. The apparatus as recited in claim 6, wherein said stress source is a chemical stress.

12. The apparatus as recited in claim 6, wherein said bodily material is blood and wherein a higher optical probe signal as compared to a membrane probe signal indicates said ROX value for said molecular oxygen, and wherein a higher membrane probe signal as compared to an optical probe signal indicates said ROX value for said bundled nitric oxide.

13. A method for controlling the concentrations of ROX and BOX, comprising the steps of:
- providing at least one optical sensor and one membrane sensor that are operatively connected to a processor;
- providing a sample including an amount of bodily material with an amount of molecular oxygen and nitric oxide, said optical sensor adapted to detect said molecular oxygen over time and to send a signal to said processor as to the amount of said molecular oxygen an said membrane sensor adapted to detect said molecular oxygen and said nitric oxide over time and to send signals to said processor over time as to the amount of said molecular oxygen and said nitric oxide;
- determining by said processor with said optical and membrane sensors baseline values for said amount of said molecular oxygen and said nitric oxide at a first point in time;
- providing a stress source;
- introducing by said stress source a stress into said sample after said baseline values are determined;
- determining by said processor with said optical and membrane sensors BOX values for said molecular oxygen and said nitric oxide at a second point in time, said BOX values being a measurement of the rate at which said molecular oxygen and said nitric oxide is consumed, respectively, in said sample after said stress is introduced;
- determining by said processor with said optical and membrane sensors ROX values for said molecular oxygen and said nitric oxide following said second point in time, said ROX values being an increase in the amount of said molecular oxygen and said nitric oxide, respectively, following said determination of said BOX values, wherein said ROX values for said molecular oxygen and said nitric oxide are determined from the difference in said optical sensor signal and said membrane sensor signal;
- determining by said processor with said optical and membrane sensors a SOX value for said molecular oxygen or said nitric oxide following said second point in time, said SOX value being a sharp increase in said molecular oxygen or said nitric oxide as compared to said ROX values for said molecular oxygen and said nitric oxide, respectively;
- introducing a controlling or blocking material into said sample, wherein said controlling material is adapted to alter either said ROX values or said BOX values in said sample; and
- administering said sample into a subject upon said determination by said processor of said SOX value.

14. A method for predicting the onset of rejection to a treatment material, comprising the steps of:
- providing an optical sensor and a membrane sensor connected to a processor;
- providing a sample from a patient intending to undergo treatment by a treatment material, including an amount of bodily material with an amount of molecular oxygen and nitric oxide, wherein said optical sensor is adapted to sense molecular oxygen over time and to send a series of signals over time to said processor relating to said amount of said molecular oxygen, and wherein said membrane sensor is adapted to sense molecular oxygen and nitric oxide over time and to send a series of signals over time to said processor relating to said amount of said molecular oxygen and said nitric oxide;
- determining by said processor with said optical and membrane sensors baseline values for said molecular oxygen and nitric oxide;
- introducing a stress into said sample following said determination of said baseline values, wherein said stress includes an amount of treatment material, and wherein said treatment material is a material that is integral to said treatment;
- determining by said processor with said optical and membrane sensors BOX values for said molecular oxygen and nitric oxide in said sample, which are a measurement of the consumption of said amount of molecular oxygen and nitric oxide, respectively, following said introduction of said stress, in said sample;
- determining by said processor with said optical an membrane sensors ROX values for said molecular oxygen and said nitric oxide, which are a measurement of an increase in said molecular oxygen and said nitric oxide, wherein said ROX value for each said molecular oxygen and said nitric oxide is determined from the difference in said optical sensor signal and said membrane sensor signal at any point in time following said determination of said BOX values in said sample;
- determining by said processor with said optical and membrane sensors a SOX value for said molecular oxygen or said nitric oxide following said second point in time, said SOX value being a sharp increase in said molecular oxygen or said nitric oxide as compared to said ROX values for said molecular oxygen and said nitric oxide, respectively;
- predicting the onset of rejection to said treatment material, wherein said predicting step is done by comparing said BOX and ROX values to the BOX and ROX values based on data obtained from individuals other than said patient, wherein said ROX and BOX values of said patient are outside of the range of said ROX and BOX values of said individuals; and
- administering said sample to said patient upon said determining by said processor of said SOX value.

15. An apparatus for measuring ROX and BOX in a sample having an amount of molecular oxygen and nitric oxide and subjected to a stress source, comprising:
- a first sensor and a second sensor in a cell that are operatively connected to a processor, wherein said first sensor is adapted to detect unbound molecular oxygen, which is molecular oxygen that is not bound to hemoglobin or white blood cells, in a sample contained in said cell, well or structure, and to deliver a signal over time as to the amount of said unbound molecular oxygen from said sample to said processor through a first data line, wherein said second sensor is adapted to detect unbound molecular oxygen and unbound nitric oxide, which is nitric oxide that is not bound to hemoglobin or white blood cells, in said sample and to deliver signals over time as to the amount of said unbound molecular oxygen and unbound nitric oxide from said sample to said processor through a second data line, wherein said processor is adapted to compute BOX, ROX and SOX values for molecular oxygen and nitric oxide in said sample, respectively, wherein said BOX value for each said molecular oxygen and said nitric oxide is a measurement of the rate said molecular oxygen and said nitric oxide become bundled by white blood cells in said sample of blood based on a detected decrease in said unbound oxygen and said unbound nitric oxide over time when said sample is subjected to a stress by a stress source, wherein said ROX value for each said molecular oxygen and nitric oxide is a measurement of the amount of bundled molecular oxygen and bundled nitric oxide in said sample based on a detected increase in said unbound molecular oxygen and said unbound nitric oxide at any point in time after said BOX value is computed, wherein said processor computes said ROX values for said molecular oxygen and said nitric oxide by determining the difference between said first sensor signal and said second sensor signal, wherein said SOX value is a measurement of a sharp increase in said nitric oxide or molecular oxygen as compared to said ROX value for nitric oxide and molecular oxygen at any point in time after said BOX value is computed, and wherein upon detection of said sharp increase, said sample is administered to a subject.

* * * * *